(12) United States Patent
Grass et al.

(10) Patent No.: US 10,045,749 B2
(45) Date of Patent: Aug. 14, 2018

(54) X-RAY SYSTEM, IN PARTICULAR A TOMOSYNTHESIS SYSTEM AND A METHOD FOR ACQUIRING AN IMAGE OF AN OBJECT

(71) Applicant: KONINKLIJKE PHILIPS N.V., Eindhoven (NL)

(72) Inventors: Michael Grass, Buchholz in der Nordheide (DE); Klaus Erhard, Hamburg (DE); Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 178 days.

(21) Appl. No.: 15/028,041

(22) PCT Filed: Oct. 13, 2014

(86) PCT No.: PCT/EP2014/071824
§ 371 (c)(1),
(2) Date: Apr. 8, 2016

(87) PCT Pub. No.: WO2015/058980
PCT Pub. Date: Apr. 30, 2015

(65) Prior Publication Data
US 2016/0249872 A1 Sep. 1, 2016

(30) Foreign Application Priority Data

Oct. 22, 2013 (EP) ...................................... 13189632

(51) Int. Cl.
*A61B 6/04* (2006.01)
*A61B 6/00* (2006.01)
(Continued)

(52) U.S. Cl.
CPC ............. *A61B 6/4452* (2013.01); *A61B 6/025* (2013.01); *A61B 6/06* (2013.01); *A61B 6/4233* (2013.01);
(Continued)

(58) Field of Classification Search
CPC ....... A61B 6/4452; A61B 6/502; A61B 6/025; A61B 6/5241; A61B 6/4266; A61B 6/06;
(Continued)

(56) References Cited

U.S. PATENT DOCUMENTS 5,526,394 A 6/1996 Siczek
6,035,013 A 3/2000 Orava
(Continued)

FOREIGN PATENT DOCUMENTS

JP S63243851 10/1988
JP 2002291727 10/2002
(Continued)

OTHER PUBLICATIONS

Ballabriga et. al. The Medipix3RX: a high resolution, zero dead-time pixel detector readout chip allowing spectroscopic imaging, Journal of Instrumentation, 8, pp. C02016, (2013).
(Continued)

*Primary Examiner* — Courtney Thomas
(74) *Attorney, Agent, or Firm* — Larry Liberchuk (57) ABSTRACT

An X-ray system (2) for acquiring an image of an object has an X-ray detector (8), which is segmented into a plurality of neighboring detector tiles. In particular, the image can be a two-dimensional projection image but also a three-dimensional volume of the object reconstructed from a tomosynthesis acquisition. An X-ray detector moving mechanism (18) is adapted for moving the X-ray detector (8) at least between a first X-ray detector position and a second X-ray detector position during operation of the X-ray system. An
(Continued)

X-ray source (4), a collimator (22) and the X-ray detector (8) of the X-ray system (2) are adapted for acquiring a plurality of partial X-ray images through the adjacent detector tiles while irradiating the object with X-ray beams from a plurality of tomographic angles $\alpha$. The processing unit is adapted for generating a two-dimension image of the object and/or for reconstructing a three-dimensional volume of the object from the acquired partial images.

20 Claims, 4 Drawing Sheets

(51) Int. Cl.
    *A61B 6/02*     (2006.01)
    *G01T 1/24*     (2006.01)
    *A61B 6/06*     (2006.01)

(52) U.S. Cl.
    CPC .......... *A61B 6/4241* (2013.01); *A61B 6/4266* (2013.01); *A61B 6/4291* (2013.01); *A61B 6/482* (2013.01); *A61B 6/502* (2013.01); *A61B 6/5241* (2013.01); *G01T 1/243* (2013.01)

(58) Field of Classification Search
    CPC ... A61B 6/4291; A61B 6/4233; A61B 6/4241; G01T 1/243
    USPC .......................................................... 378/37
    See application file for complete search history.

(56) References Cited

U.S. PATENT DOCUMENTS

| | | | | |
|---|---|---|---|---|
| 7,302,031 | B2* | 11/2007 | Hjarn | A61B 6/02 378/23 |
| 7,342,233 | B2* | 3/2008 | Danielsson | A61B 6/4241 250/370.09 |
| 7,590,217 | B2 | 9/2009 | Strommer | |
| 8,497,484 | B2 | 7/2013 | Chmeissani | |
| 9,460,822 | B2* | 10/2016 | Danielsson | A61B 6/06 |
| 2003/0155518 | A1 | 8/2003 | Francke | |
| 2008/0267484 | A1* | 10/2008 | Chen | A61B 6/032 382/132 |

FOREIGN PATENT DOCUMENTS

| | | | |
|---|---|---|---|
| JP | 2012245329 A | * | 12/2012 |
| JP | 2012245329 A | | 12/2012 |
| WO | 1995015072 | | 6/1995 |
| WO | 2004/038810 | | 5/2004 |
| WO | 2013004574 | | 1/2013 |

OTHER PUBLICATIONS

Aslund et. al. Physical characterization of a scanning photon counting digital mammography system based on Si-strip detectors, Med. Phys. 34(6), 1918-1925,(2007).

* cited by examiner

X-RAY SYSTEM, IN PARTICULAR A TOMOSYNTHESIS SYSTEM AND A METHOD FOR ACQUIRING AN IMAGE OF AN OBJECT

CROSS REFERENCE TO RELATED APPLICATIONS

This application is the U.S. National Phase application under 35 U.S.C. § 371 of International Application No. PCT/EP2014/071824, filed Oct. 13, 2014, published as WO 2015/058980 on Apr. 30, 2015, which claims the benefit of European Patent Application Number 13189632.6 filed Oct. 22, 2013. These applications are hereby incorporated by reference herein.

FIELD OF THE INVENTION

The invention relates to an X-ray system and in particular to a tomosynthesis system for acquiring an image of an object as well as a method for acquiring an image of an object.

BACKGROUND OF THE INVENTION

In order to detect and analyze breast cancer, various mammography systems are known.

Besides conventional mammography screening systems (planar mammography), which require compressing the female breast between two plates and which are used for creating two-dimensional X-ray images with a high lateral resolution, digital breast tomosynthesis (DBT) mammography systems are known, that also realize depth resolution and relax the requirement of strongly compressing the breast during examination, as well as breast computer tomography (CT) systems.

In planar mammography currently energy resolving photon counting detectors of sufficient size for mammography are unavailable. Due to the large volume irradiated when acquiring a projection image a scatter grid is necessary for reducing scatter in the projection images.

In DBT systems, a plurality of X-ray images may be acquired while the breast is irradiated with an X-ray beam from a plurality of tomographic angles. Conventionally, an X-ray source is moved along a circular arc path while being always oriented towards a fixed detector above which the breast is supported. Conventionally, X-ray images are acquired within a range of tomographic angles of exemplarily up to 2×25°. From the plurality of acquired two-dimensional X-ray images, a final three-dimensional volume of the breast may be generated. Such a three-dimensional volume may provide for both, good lateral resolution and sufficient depth resolution, wherein the depth resolution typically increases reciprocally proportional with the range of tomographic angles.

Multi-slit X-ray scanning systems are known, which comprise a detector having a plurality of detector strips and associated read-out electronics. A pre-collimator having multiple slits at the projections of these detector strips is provided. A further collimator is placed between breast and detector to remove radiation that is scattered in the tissue.

However, it may be difficult to design a multi-slit scanning system which is able to perform a large angle tomosynthesis scan and a projection mammography at the same time. Furthermore, breast biopsies may be hard to realize on these systems since a necessary pre-collimator may hamper the installation of a biopsy unit in the most natural position.

Also, high tube power is required since the pre-collimator limits the tube output to the detector lines of the photon counting detector.

SUMMARY OF THE INVENTION

A significant reduction of the total scan time as well as an improved usage of the available X-ray flux would constitute a great advantage for a multi-slit scanning system. Additionally, the removal of a pre-collimator for multi-slit scanning systems would constitute a further advantage for being able to easily integrate a biopsy unit. The object of the invention therefore lies in proposing an improved mammography system having the above mentioned advantages.

The object is met by an X-ray system comprising the features of claim 1. Advantageous embodiments and further improvements may be derived from the subclaims and the following description.

An X-ray system and in particular a tomosynthesis system for acquiring an image of an object is proposed, the system comprising an X-ray source, an X-ray detector, a collimator, an X-ray source moving mechanism, an X-ray detector moving mechanism and a processing unit. The X-ray source moving mechanism is adapted for moving the X-ray source into different tomographic angles $\alpha$ relative to a detection surface of the X-ray detector. The X-ray detector is segmented into a plurality of neighboring detector tiles. In the following, X-ray detector segments and detector tiles are equivalents. The X-ray detector moving mechanism is adapted for moving the X-ray detector at least between a first X-ray detector position and a second X-ray detector position during operation of the tomosynthesis system. The X-ray system, i.e. the X-ray source, the collimator and the X-ray detector, are adapted for acquiring a plurality of partial X-ray images through all detector tiles while irradiating the object with X-ray beams from a plurality of tomographic angles $\alpha$, wherein the processing unit is adapted for reconstructing an image of the object from the acquired partial images. In particular, the image is a three-dimensional volume, but may also be a two-dimensional image.

The X-ray source may be any conventional X-ray source, which provides an X-ray beam with defined characteristics, e.g. through a rotating anode tube.

The X-ray detector of the tomosynthesis system according to the invention is segmented into single detector tiles, which are arranged by columns and/or rows of detector arrays, which have a high resolution. With a simple translation of the segmented X-ray detector and two acquisitions, all segments may be impinged by X-ray beams and the complete detector plane may be covered, i.e. columns or rows of detector arrays may switch their positions in the projection plane. In this regard, it is feasible to build photon counting, energy resolving detector arrays with limited size instead of single line detectors of the same type. These detector arrays are very efficient with respect to X-ray detection and characterization.

A gist of the invention therefore lies in providing an X-ray system and in particular a tomosynthesis system with photon-counting detector arrays for conducting mammography screening that allows for acquiring energy-resolved X-ray images at reduced scatter level compared to flat-panel detector systems as well as a distinct efficiency and the ability to measure the energy of impinging photons. Still, a reconstruction of a three-dimensional volume is possible and, furthermore, a pre-collimator is not necessary, such that a biopsy unit may still be integrated into the tomosynthesis system between the collimator and the X-ray detector and such that the X-ray flux may be increased. Segmenting the X-ray detector into detector tiles may also allow to provide a larger detector plane than possible with commercially available photon counting X-ray detectors.

The X-ray source moving mechanism may be adapted for moving the X-ray source along an arcuate path in order to irradiate an object to be observed from a plurality of tomographic angles. The distance between all points on the arcuate path and a center of the detector plane may be constant.

The X-ray detector moving mechanism may furthermore be adapted for providing a linear motion of the X-ray detector especially parallel to a common detector plane. However, in order to prevent that the X-ray beam impinges the X-ray detector perpendicularly only at a tomographic angle of 0°, the X-ray detector moving mechanism may be adapted for tilting/rotating the X-ray detector around an axis perpendicular to the X-ray beam. Thereby, it may be ensured that the X-ray beam exclusively impinges perpendicularly onto the segments of the X-ray detector plane. In other words, while the X-ray source may be positioned at various locations along an arcuate path in order to irradiate the object to be examined from various tomographic angles α, a positioning of the X-ray detector is adjusted such that, independent of the selected tomographic angle α, the X-ray beam is perpendicular to the detection surface of the X-ray detector.

In an advantageous embodiment, the first X-ray detector position and the second X-ray detector position are shifted in a common projection plane about the width of a detector tile or less. Consequently, the X-ray detector may comprise a plurality of parallel arranged detector tiles, wherein delimiting edges of neighboring detector tiles are distanced to each other, wherein the distance is the width of a detector tile or less. By simply moving the X-ray detector about this distance, in a second acquisition process the remaining part of the detector is used, such that altogether the complete detector plane has been exposed to the X-ray beams.

In a still further advantageous embodiment, two neighboring detector tiles provide an overlap region between partial image acquisitions, wherein the X-ray system further comprises a beam shaper, which is adapted for adjusting the X-ray beam intensity in the overlap region. By slightly overlapping two adjacent image acquisition regions, image reconstruction is improved. In the overlap region, basically the same narrow image sections are acquired twice, which allows to seamlessly connect two adjacent image sections much more accurate.

Still further, the X-ray system may be adapted for moving the X-ray detector by means of the X-ray detector moving mechanism from the first X-ray detector position to the second X-ray detector position at the same tomographic angle α and the X-ray system may be adapted for acquiring a partial image at each of the first X-ray detector position and the second X-ray detector position for each of a plurality of discrete tomographic angles α. Consequently, for each tomographic angle α, two partial images are acquired and combined for conducting the reconstruction. This leads to a clearly improved quality of the reconstructed image and the exposure to X-ray radiation is comparable to common methods. The reconstruction may be conducted through a filtered back projection algorithm.

However, in a further advantageous embodiment, the X-ray system is adapted for continuously acquiring partial X-ray images over the distance between the first X-ray detector position and the second X-ray detector position. Hence, a plurality of images is acquired in intermediate positions. This may be advantageous for achieving a better noise homogeneity in the resulting two-dimensional image.

Alternatively, the X-ray system may be adapted for moving the X-ray detector by means of the X-ray detector moving mechanism from the first X-ray detector position to the second X-ray detector position at the same time the tomographic angle α is changed and the X-ray system may be adapted for acquiring a partial image either at the first X-ray detector position or the second X-ray detector position for each of a plurality of discrete tomographic angles α. Hereby, the total number of exposures to X-ray radiation may be clearly reduced. However, the effort for reconstructing a three-dimensional image from such a set of data may require an iterative reconstruction method.

It goes without saying, that the collimator should be adjusted and/or moved corresponding to the motion of the X-ray detector.

In a still further embodiment, the collimator comprises a set of perpendicular line collimation devices on top of each other, which is adapted for generating inverted chessboard patterns with partial image acquisitions. This allows to extend the direction of the partial scans to the chest-mammilla direction from view to view. With this pattern, the linear partial images are interrupted, i.e. gaps occur in x- and y-direction of the detector plane. For providing a full exposure of the detector plane, two orthogonal line collimators may be positioned exemplarily in two different positions for each of two detector positions. Hence, four partial images are created. This leads to a further reduction of scatter effects as well as a possible reduction of detector size.

In a further advantageous embodiment, the X-ray system comprises an anti-scatter grid arranged between the X-ray detector and a support arrangement for supporting the object to be examined. An anti-scatter grid may be useful if relatively large tissue volumes are to be screened. The anti-scatter grid is to be understood as a device for limiting the amount of radiation scatter created in an X-ray exposure reaching the detector. Usually, such a grid comprises a series of alternating parallel strips of lead and a radio lucent material, which basically only lets parallel arranged X-ray beams pass through the radiolucent regions. Scattered radiation may not pass the grid. The scatter grid may preferably comprise a one-dimensional scatter grid per detector tile.

Still further, the X-ray detector tiles may be connected with the X-ray source moving mechanism through a gear such that each single X-ray detector tile is rotated synchronously with a focus of the X-ray source during an image acquisition, in particular a tomosynthesis acquisition. Hereby, it is ensured that the X-ray beams impinge perpendicularly onto the X-ray detector tiles. The image acquisition quality may thereby be clearly improved. In this way, each tomosynthesis projection is acquired with an optimal orthogonal orientation of the detector unit while the space requirements for the detector rotation are defined by the detector tile width and hence only minimal compared to a rotation of a flat panel detector. In other words, while the X-ray source may be positioned at various locations along e.g. an arcuate path in order to irradiate the object to be examined from various tomographic angles α, a positioning of the X-ray detector is adjusted such that, independent of the selected tomographic angle α, the X-ray beam is perpendicular to the detection surface of the detector. In this regard, the expression "perpendicular" is to be understood that a direction of the X-ray beam is normal to a plane of the X-ray detector surface.

The X-ray system may be adapted for acquiring partial X-ray images within a range of tomographic angles of more than +/−25°. It is in combination with the increased image quality together with this tomographic angle range a high quality reconstruction of a three-dimensional volume is possible.

The X-ray system may be easily extended to a multi-slit scanning system acquiring N partial projections, such that detector material and hence detector costs are clearly reduced.

Due to the fact that a pre-collimator is not necessary and that the collimator may be arranged very near to the X-ray source, such that there is enough space for integration of a biopsy unit between the X-ray source and the X-ray detector. Hereby, the X-ray system according to the invention has a clear advantage compared to known multi-slit scanning systems.

The invention further relates to a method for acquiring an image, in particular a three-dimensional image of an object with an X-ray system, in particular a tomosynthesis system, the X-ray system having a segmented X-ray detector unit, comprising the steps of:

a) acquiring a first image at a first detector position and at a first tomographic angle such that a first set of detector tiles is exposed to an X-ray beam of an X-ray source,
b) moving the X-ray detector unit from the first position into a second position by means of the X-ray detector unit moving mechanism,
c) acquiring a second image at the second detector position and the first tomographic angle or a second tomographic angle such that a second set of detector tiles is exposed to an X-ray beam of an X-ray source, repeating a) to c) for remaining tomographic angles of a predetermined set of tomographic angles such that a set of N two-dimensional images is acquired, and
d) reconstructing an image, in particular a three-dimensional volume based on the N two-dimensional images.

As explained above, the method may provide a set of partial images corresponding to a set of detector segments at each of the first X-ray detector position and the second X-ray detector position for each of a plurality of discrete tomographic angles α. As an alternative, the partial images may be acquired for different tomographic angles. While the first alternative requires a reconstruction algorithm such as a filtered-back projection algorithm, the second alternative may be reconstructed with an iterative reconstruction algorithm.

The first and second alternative are distinguished by the further movement step of the X-ray source from a first tomographic angle to a second tomographic angle. It goes without saying that the method steps are repeatedly conducted until all partial images at the predetermined range of tomographic angles are acquired.

It is to be noted that aspects and embodiments of the present invention are described herein partly with respect to the X-ray system and its structural or functional features and partly with respect to a possible mode of use of such X-ray system, which may also include two-dimensional imaging. However, a person skilled in the art will gather from the above and the following description that, unless other notified, in addition to any combination of features belonging to one type of description also any combination between features relating to different embodiments is considered to be disclosed with this application.

BRIEF DESCRIPTION OF THE DRAWINGS

Features and advantages of the present invention will be further described with respect to specific embodiments as shown in the accompanying drawings to which the invention shall not be limited.

All figures are only schematically and not to scale. Similar features are indicated with similar or same reference signs throughout the figures.

DETAILED DESCRIPTION OF EMBODIMENTS

Figure 1:
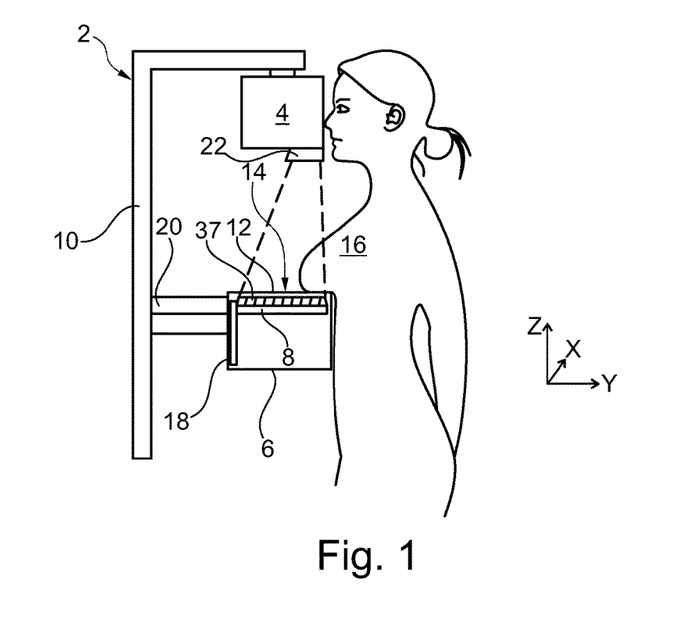
FIG. 1 shows a side view of an X-ray system and in particular a tomosynthesis system.

FIG. 1 shows a side view of an X-ray system, and in particular a tomosynthesis system 2 according to an embodiment of the present invention. An X-ray source 4 and a housing 6 comprising an X-ray detector 8 are attached to a supporting frame 10. An upper surface 12 of the housing 6 acts as a support arrangement 14 for supporting the female breast 16 to be examined during the operation of the X-ray system 2. The housing 6 may be substantially larger, for example by a factor 1.5 to 5, in its x-direction and its z-direction than the X-ray detector 8 installed therein, which allows to move the X-ray detector 8 within the housing 6.

Figure 5:
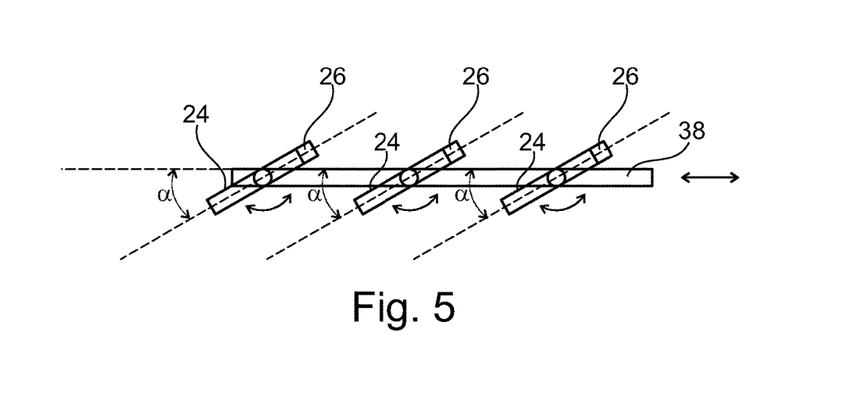
FIG. 5 shows a tilting mechanism of X-ray detector tiles.

The housing 6 may also comprises an X-ray detector moving mechanism 18 which is adapted to move the X-ray detector 8 along the x- or y-direction indicated with a schematically shown coordinate system. Also, the X-ray detector 8 may be moved on a pivoting motion path, e.g. about the y-axis. Additionally, each detector segment may be moved on a pivoting path as illustrated in FIG. 5. Furthermore, as will be described further below, the X-ray detector 8 may be provided with an anti-scatter grid which, when its use is not desired, may be displaced into a parking position within an extension 20 of the housing 6.

The X-ray source 4 furthermore comprises a collimator 22, which is adapted to filter a set of X-ray beams so that only those oriented towards the detector segments are allowed through. The collimator 22 in this case creates a pattern of rays that impinge onto detector tiles of the X-ray detector 8 further explained below.

Figure 2A:
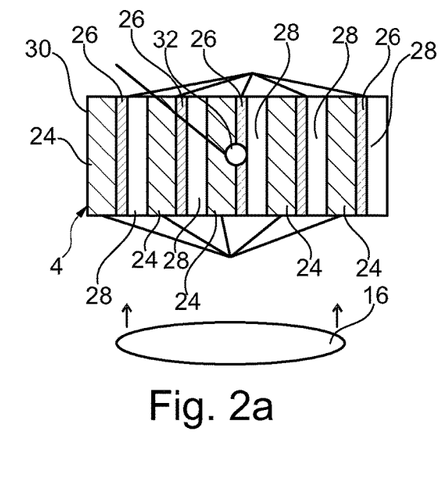
FIGS. 2a and 2b show the general setup of the X-ray detector.
Figure 2B:
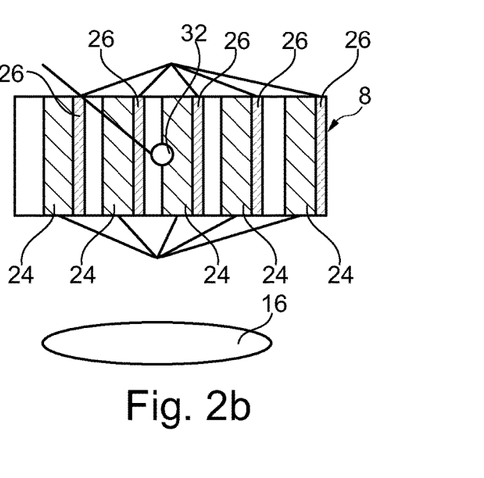

FIGS. 2a and 2b demonstrate the general setup of the detector 8, which consists of a plurality of detector tiles 24 equipped with readout electronics 26, which are exemplarily located at a lateral delimitation of each of the detector tiles 24. Such detector units are commercially available with readout electronics attached to a lateral delimitation instead of an installation on the back of the respective detector unit.

Between all detector tiles 24 and the associated readout electronics 26, gaps 28 are present. The size of a gap 28 plus a readout electronic 26 approximately equals the width of a detector tile 24 without the readout electronics. The active detector surface therefore equals approximately a half of the surface of the projection plane 30, which is the rectangular area that encloses all detector tiles 24, readout electronic 26 and gaps 28.

The object to be examined, i.e. breast 16, is located above the detector 8 in the drawing plane.

Exemplarily, the detectors 8 in FIG. 2a and FIG. 2b are exactly the same, but moved in a translational direction relative to a source 32, which resembles a source position of an X-ray system under a tomographic angle α. In FIG. 2a, the left half of source 32 is situated above the third detector tile 24 from the left and the right half is situated above a readout electronics 26. In FIG. 2b, the left half of source 32 is located above a gap 28 and the right half is situated above the third detector tile 24 from the left. Altogether, by acquiring two partial images with a detector 8 as shown in FIGS. 2a and 2b, a full image can be reconstructed by using the two partial images. This allows to connect a plurality of detector units with a high resolution but smaller detector area than usual mammography or tomosynthesis systems.

FIGS. 2a and 2b further resemble a first exemplary embodiment, in which two partial projections $p_1(\alpha)$ and $p_2(\alpha)$ are acquired with a multi-slit mammography system with a detector configuration which covers the full projection plane 30 after one detector displacement. Both partial projections $p_1(\alpha)$ and $p_2(\alpha)$ are acquired per source position and yield together a full 2D projection image $p(\alpha)$ in projection plane 30. A tomosynthesis reconstruction may be conducted through a filtered back projection of the series of two-dimensional projections $p(\alpha_1), \ldots, p(\alpha_n)$ under a given set of tomographic angles $\alpha_1, \ldots, \alpha_n$.

Figure 3A:
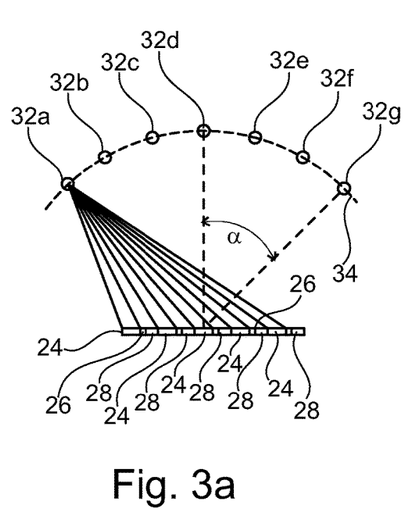
FIGS. 3a and 3b show exposures at different tomographic angles.
Figure 3B:
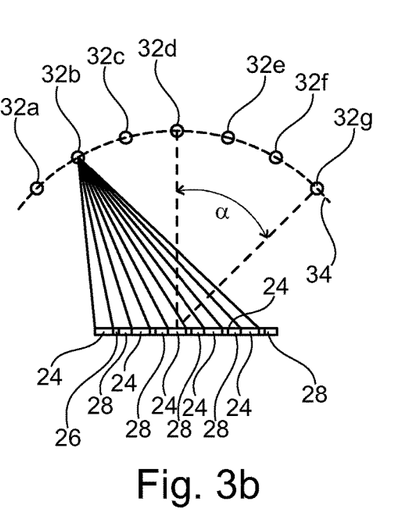

Another exemplary embodiment is shown with FIGS. 3a and 3b. Here, several different source positions 32a-32g are shown. The different source positions 32a-32g are situated along an arcuate path 34. While the central source position 32d leads to an angle α of 0°, the outermost source positions 32a and 32g lead to a tomosynthesis angle α of approximately ±30°. In this exemplary embodiment, two partial projections with different detector displacement are acquired from the neighboring source positions 32a and 32b. For this acquisition scheme, an iterative reconstruction method is required to compute a 3D tomosynthesis volume from a series of partial projections from the different source positions 32a-32g.

Figure 4A:
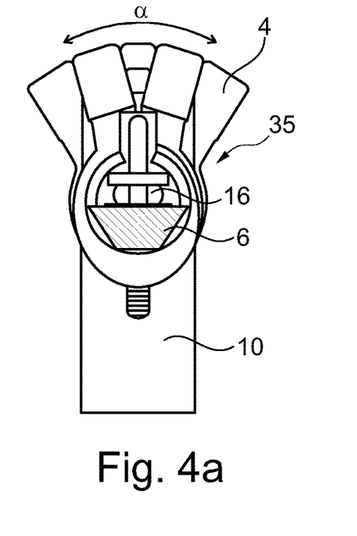
FIGS. 4a and 4b show the X-ray source moving mechanism.
Figure 4B:
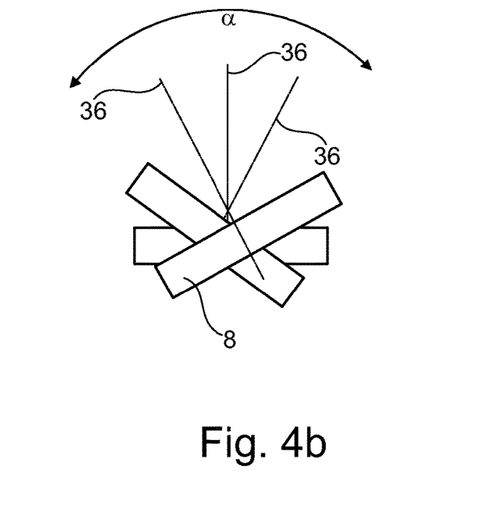

In a front view shown in FIGS. 4a and 4b, a pivoting motion of the X-ray source 4 through an X-ray moving mechanism 36 is schematically illustrated. The X-ray source 4 may be arranged at various locations along the arcuate path 34 as shown in FIGS. 3a and 3b in order to irradiate the female breast 16 under a plurality of tomographic angles α.

Together with the motion of the X-ray source 4 also the X-ray detector 8 may be moved within the housing 6 guided by the X-ray detector moving mechanism 18. Therein, depending on the prevailing tomographic angle α, which is shown to be in a range of 0° to e.g. ±45°, the detector 8 is pivoted into such an orientation that an X-ray beam coming from the X-ray source 4 impinges with its center axis 36 perpendicular to a detection surface of the X-ray detector 8. As an alternative, the detector tiles 24 may be pivotable individually, as shown in FIG. 5.

Furthermore, FIG. 5 demonstrates that single detector tiles 24, e.g. with attached readout electronics 26, may each be connected to a gear 38, which in turn is connected to an X-ray source moving mechanism 35. Consequently, each of the detector tiles 24 may be tilted/pivoted according to the tomographic angle α, such that X-ray beams always impinge perpendicularly onto the detector tiles 24.

Figure 6A:
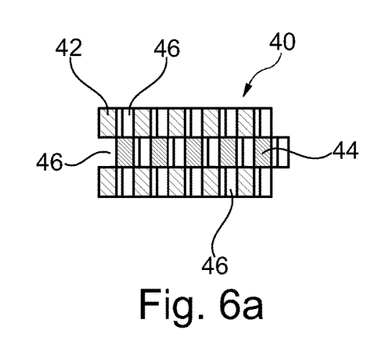
FIGS. 6a, 6b, 6c and 6d shown a detector with a chessboard pattern in two different positions as well as corresponding collimator positions.
Figure 6B:
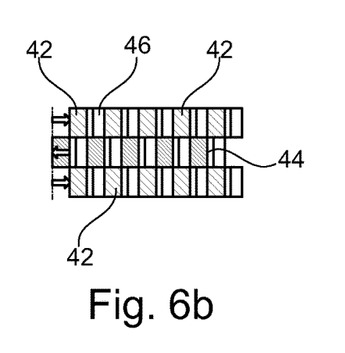
Figure 6C:
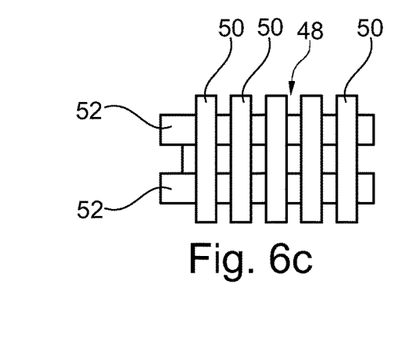
Figure 6D:
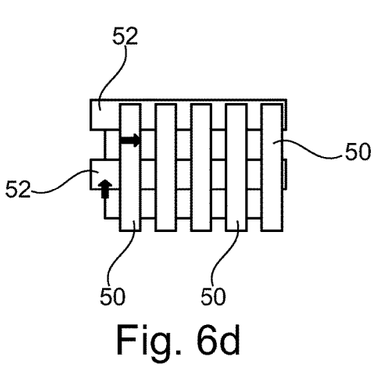

In FIGS. 6a, 6b, 6c and 6d it is demonstrated how to use a detector 40 with a chessboard pattern with neighboring strip-like detector tiles 42 and 44. FIG. 6a demonstrates a first position of the detector tiles 42 and 44, wherein the linear images acquired by the detector tiles 42 and 44 are interrupted, such that gaps 46 occur. In FIG. 6b the detector tiles 42 and 44 are translated as illustrated with the arrows in FIG. 6b into an inverted chessboard pattern position such that the gaps of FIG. 6a correspond to the detector tile positions of FIG. 6b and vice versa. The collimator 48 comprises a set of perpendicular line collimation devices 50 and 52 on top of each other, which are adapted for generating inverted chessboard patterns with partial image acquisitions. A first collimator position shown in FIG. 6c corresponds to the first detector position shown in FIG. 6a, while a second collimator position shown in FIG. 6d corresponds to the second detector position shown in FIG. 6b. This leads to a further reduction of scatter effects as well as a possible reduction of detector size.

Figure 7:
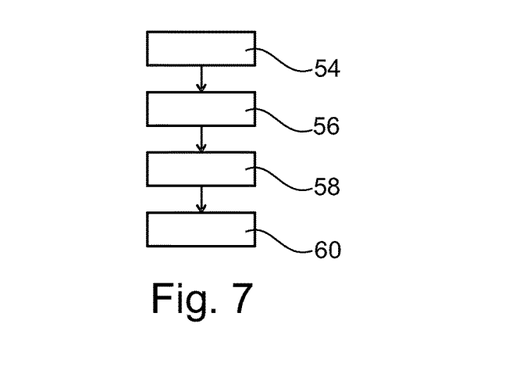
FIG. 7 shows the method according to the invention.

FIG. 7 schematically shows a method according to the invention comprising the steps of acquiring 54 a partial image and moving 56 an X-ray detector from a first position to a second position. The method according to the invention further comprises the step of moving 58 an X-ray source along an arcuate path. Furthermore, the method comprises the step of reconstructing 60 an image, in particular a three-dimensional volume based on the acquired partial images.

It should be noted that the term "comprising" does not exclude other elements or steps and that the indefinite article "a" or "an" does not exclude the plural. Also elements described in association with different embodiments may be combined. It should also be noted that reference signs in the claims shall not be construed as limiting the scope of the claims.

LIST OF REFERENCE SIGNS

2 X-ray/tomosynthesis system
4 X-ray source
6 Housing
8 X-ray detector
10 Supporting frame
12 Upper surface
14 Support arrangement
16 Female breast
18 X-ray detector moving mechanism
20 Extension of the housing 6
22 Collimator
24 Detector tile
26 Readout electronics
28 Gap
30 Projection plane
32, 32a-32g Source (positions)
34 Arcuate path
36 X-ray source moving mechanism
38 Gear
40 X-ray detector
42 X-ray detector tile
44 X-ray detector tile
46 Gap
48 Collimator
50 Collimation device
52 Collimation device
54 Acquiring a partial image
56 Moving an X-ray detector
58 Moving an X-ray source
60 Reconstructing a three-dimensional volume
α Tomographic angle

The invention claimed is:
1. A mammography X-ray system for acquiring an image of an object, the system comprising:
an X-ray source,
an X-ray detector,
a collimator,
an X-ray source moving mechanism, an X-ray detector moving mechanism, and a processing unit, wherein the X-ray source moving mechanism is adapted for moving the X-ray source into different tomographic angles α relative to a detection surface of the X-ray detector, wherein the X-ray detector is segmented into a plurality of neighboring detector tiles wherein delimiting edges of neighboring detector tiles are distanced to each other, wherein the distance is the width of a detector tile or less, wherein the X-ray detector moving mechanism is adapted for moving the X-ray detector at least between a first X-ray detector position and a second X-ray detector position during operation of the X-ray system, and wherein the X-ray source, the collimator and the X-ray detector are adapted for acquiring a plurality of partial X-ray images through the neighboring detector tiles while irradiating the object with X-ray beams from a plurality of tomographic angles α, wherein the processing unit is adapted for reconstructing an image of the object from the acquired partial images.

2. The X-ray system of claim 1, wherein the image of the object to be reconstructed is a three-dimensional volume of the object.

3. The X-ray system of claim 1, wherein the first X-ray detector position and the second X-ray detector position are shifted in a common projection plane about the width of a detector tile or less.

4. The X-ray system of claim 3, wherein two neighboring detector tiles provide an overlap region between partial image acquisitions of the first X-ray detector position and the second X-ray detector position, wherein the X-ray system further comprises a beam shaper, which is adapted for adjusting the X-ray beam intensity in the overlap region.

5. The X-ray system of any claim 1, wherein the X-ray system is adapted for moving the X-ray detector by means of the X-ray detector moving mechanism from the first X-ray detector position to the second X-ray detector position at the same tomographic angle α and wherein the X-ray system is adapted for acquiring a partial image at each of the first X-ray detector position and the second X-ray detector position for each of a plurality of discrete tomographic angles α.

6. The X-ray system of any of claim 1, wherein the X-ray system is adapted for continuously acquiring partial images over the distance between the first X-ray detector position and the second X-ray detector position.

7. The X-ray system of any of claim 1, wherein the X-ray system is adapted for moving the X-ray detector by means of the X-ray detector moving mechanism from the first X-ray detector position to the second X-ray detector position at the same time the tomographic angle α is changed and wherein the X-ray system is adapted for acquiring a partial image either at the first X-ray detector position or the second X-ray detector position for each of a plurality of discrete tomographic angles α.

8. The X-ray system of claim 7, wherein the reconstruction is conducted by an iterative reconstruction method.

9. The X-ray system of claim 1, wherein the collimator is adapted for adjusting a collimation pattern to the tomographic angle α and the X-ray detector position.

10. The X-ray system of claim 1, wherein the collimator comprises a set of perpendicular line collimation devices on top of each other, which generate inverted chessboard patterns for the acquisition of two different partial images.

11. The X-ray system of claim 1, further comprising an anti-scatter grid arranged between the X-ray detector and a support arrangement for supporting the object to be examined.

12. The X-ray system of claim 1, wherein the X-ray detector tiles are connected with the X-ray source moving mechanism through a gear such that each single X-ray detector tile is rotated synchronously with a focus of the X-ray source during an image acquisition.

13. The X-ray system of claim 1, further comprising a biopsy unit between the X-ray source and the X-ray detector.

14. A method for acquiring an image of an object with a mammography X-ray system having a segmented X-ray detector with neighboring detector tiles with delimiting edges separated by a width of a detector tile or less, comprising the steps of:

acquiring a first image at a first detector position and at a first tomographic angle such that a first set of the detector tiles is exposed to an X-ray beam of an X-ray source;

moving the X-ray detector from the first position into a second position and moving the X-ray source from the first tomographic angle into a second tomographic angle;

acquiring a second image at the second detector position and the second tomographic angle such that a second set of the detector tiles is exposed to an X-ray beam of an X-ray source; and reconstructing the image of the object from the acquired first and second images.

15. The method of claim 14, further comprising:

continuously acquiring partial images over a distance between the first X-ray detector position and the second X-ray detector position.

16. The method of claim 14, further comprising:

reconstructing the image with an iterative reconstruction algorithm.

17. The method of claim 14, further comprising:

adjusting a collimation pattern to the tomographic angle α and the X-ray detector position.

18. The method of claim 14, further comprising:

rotating each X-ray detector tile synchronously with a focus of the X-ray source during an image acquisition.

19. An imaging system, comprising:

an X-ray source configured to move into different tomographic angles α relative to a detection surface of an X-ray detector, wherein the X-ray detector is segmented into a plurality of neighboring detector tiles with delimiting edges distanced to each other by a distance with a width of a detector tile or less; and an X-ray detector configured to move between a first X-ray detector position and a second X-ray detector position, wherein the X-ray source and the X-ray detector are adapted for acquiring a plurality of partial X-ray images through the neighboring detector tiles while irradiating an object with X-ray beams from a plurality of tomographic angles α.

20. The imaging system of claim 19, further comprising:

a reconstructor configured to reconstruct an image of a scanned object from the acquired partial images.

* * * * *